US009808413B2

(12) United States Patent
Abe

(10) Patent No.: US 9,808,413 B2
(45) Date of Patent: *Nov. 7, 2017

(54) RESIN BEADS, METHOD FOR MANUFACTURING RESIN BEADS AND PRODUCT CONTAINING RESIN BEADS

(71) Applicant: DAINICHISEIKA COLOR & CHEMICALS MFG. CO., LTD., Tokyo (JP)

(72) Inventor: Takashi Abe, Tokyo (JP)

(73) Assignee: DAINICHISEIKA COLOR & CHEMICALS MFG. CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/117,384

(22) PCT Filed: May 1, 2015

(86) PCT No.: PCT/JP2015/063139
§ 371 (c)(1),
(2) Date: Aug. 8, 2016

(87) PCT Pub. No.: WO2015/174305
PCT Pub. Date: Nov. 19, 2015

(65) Prior Publication Data
US 2016/0346187 A1  Dec. 1, 2016

(30) Foreign Application Priority Data
May 12, 2014 (JP) .................. 2014-098425

(51) Int. Cl.
| | | |
|---|---|---|
| *C08F 2/18* | (2006.01) | |
| *A61K 8/81* | (2006.01) | |
| *A61K 8/89* | (2006.01) | |
| *A61K 8/891* | (2006.01) | |
| *A61K 8/894* | (2006.01) | |
| *C08F 2/44* | (2006.01) | |
| *A61Q 19/00* | (2006.01) | |
| *A61K 8/86* | (2006.01) | |
| *A61K 8/02* | (2006.01) | |
| *A61Q 1/02* | (2006.01) | |

(52) U.S. Cl.
CPC ............ *A61K 8/8152* (2013.01); *A61K 8/025* (2013.01); *A61K 8/86* (2013.01); *A61K 8/89* (2013.01); *A61K 8/891* (2013.01); *A61K 8/894* (2013.01); *A61Q 1/02* (2013.01); *A61Q 19/00* (2013.01); *C08F 2/18* (2013.01); *C08F 2/44* (2013.01); *A61K 2800/10* (2013.01); *A61K 2800/412* (2013.01); *A61K 2800/594* (2013.01); *A61K 2800/624* (2013.01); *A61K 2800/654* (2013.01)

(58) Field of Classification Search
CPC .................................. C08L 33/10; C08F 2/18
See application file for complete search history.

(56) References Cited

U.S. PATENT DOCUMENTS

| | | |
|---|---|---|
| 2014/0017288 A1 | 1/2014 | Matsuhita |
| 2017/0044360 A1 | 2/2017 | Abe |

FOREIGN PATENT DOCUMENTS

| | | |
|---|---|---|
| JP | 61-073713 | 4/1986 |
| JP | 05339125 | 12/1993 |
| JP | 8-092524 | 4/1996 |
| JP | 8-104772 | 4/1996 |
| JP | 09227609 | 9/1997 |
| JP | 09255705 | 9/1997 |
| JP | 2003-073405 | 3/2003 |
| JP | 2004-002728 | 1/2004 |
| JP | 2007-100097 | 4/2007 |
| JP | 2009138034 | 6/2009 |
| JP | 2012072081 | 4/2012 |
| JP | 2013053237 | 3/2013 |
| JP | 2013227535 | 11/2013 |
| WO | 01/70826 | 9/2001 |
| WO | 2011/121821 | 10/2011 |
| WO | 2012/102296 | 8/2012 |
| WO | 2013161098 | 10/2013 |

OTHER PUBLICATIONS

JP 2013 053237 Machine translation (2013).*
JP 09 255705 Machine translation (1997).*
International Search Report for PCT/JP2015/063139, dated Jun. 9, 2015, 3 pages including English translation.
Extended European Search Report, issued in the corresponding European patent application No. 15793062.9, dated Sep. 5, 2017, 6 pages.

* cited by examiner

*Primary Examiner* — Kuo-Liang Peng
(74) *Attorney, Agent, or Firm* — Hamre, Schumann, Mueller & Larson, P.C.

(57) ABSTRACT

The present invention provides resin beads that are capable of realizing a water repellent and oil repellent effect, and further, that are also capable of providing cosmetic materials excellent in persistence of makeup when added and used in cosmetic materials etc. because the resin beads themselves contain silicone in a fixed state, and the present invention also provides a process for producing the resin beads. Resin beads being resin particles (a copolymer) obtained by subjecting a monomer mixture containing a plurality of monomers each having a copolymerizable functional group to suspension polymerization in a state where at least a nonpolymerizable silicone is present, the resin particles containing the silicon in a fixed state, and a process for producing the resin beads.

6 Claims, No Drawings

RESIN BEADS, METHOD FOR MANUFACTURING RESIN BEADS AND PRODUCT CONTAINING RESIN BEADS

TECHNICAL FIELD

The present invention relates to resin beads being resin particles containing a non-polymerizable silicone, a process for producing the resin beads, and intended purposes of the resin beads. In more detail, the present invention relates to resin beads containing a non-polymerizable silicone in a fixed state, the non-polymerizable silicone being a functional material capable of imparting water repellency and oil repellency, a process for producing the resin beads, and products in the fields that need such functionality, such as, for example, cosmetics, dermal agents including ointments and medical patches, paints, shaped articles, films, coating agents, dispersions, printing inks, inkjet inks, resin compositions, and other products.

BACKGROUND ART

Conventionally, resin beads have been used in various fields, such as a matting agent, a lubricant, and an antiblocking agent, because of the characteristics originating in the spherical shape. Furthermore, various kinds of resin powders (resin particles) have been used as makeup application in cosmetic materials in order to improve extensibility. However, these resin powders are liable to bleed due to water or sweat, thus there is a problem that makeup deterioration occurs when such bleed occurs, and when the resin powders are utilized in cosmetic materials, hydrophobization treatment has been applied to the surface of a powder in order to increase adhesion of the resin powder to skin and improve water repellency, or other purposes.

As the method of applying hydrophobization treatment to a powder, a method of applying heat treatment with an oil agent to the surface of a powder, a method of baking a methyl hydrogen polysiloxane onto a powder, and so on are known. Furthermore, there is a proposal on a powder the surface of which is coated with, for example, a silicone-acrylic-based graft copolymer in order to obtain a cosmetic material that achieves a higher functionality, that is excellent in adherence to skin and in feeling after use, that is rich in hydrophobicity, and that has a favorable persistence of makeup (see, Patent Literature 1).

Moreover, in Patent Literature 2, it is pointed out that, even though imparting water repellency, improving adherence to skin or the like, and securing compatibility with a coexisting oil agent are simultaneously required for silicone polymers that are often used in cosmetic materials, hydrophilicity is lost by introducing a long-chain alkyl group (hydrophobic group) in a silicone polymer in order to improve compatibility and on the other hand, hydrophobicity is lost by introducing a hydrophilic group in order to improve adherence, and thus it is difficult to solve the compatibility and the adherence simultaneously. Against the problem, there is a proposal on a copolymer obtained by copolymerizing four kinds of different monomer units each containing a particular amount of a silicone macromonomer having a particular structure.

CITATION LIST

Patent Literature

Patent Literature 1: Japanese Patent Laid-Open No. 5-339125

Patent Literature 2: Japanese Patent Laid-Open No. 2012-072081

SUMMARY OF INVENTION

Technical Problem

However, in the method of baking a methyl hydrogen polysiloxane, there has been a problem that the surface treatment becomes ununiform depending on the kind of resin beads used or the reaction condition, and there has also been a problem that the resin is deteriorated by heat depending on the baking temperature. Moreover, according to studies conducted by the present inventor, in the method of coating the powder surface with the silicone-acrylic-based graft copolymer, which is proposed in Patent Literature 1, adsorption is not sufficient in some cases depending on the powder and the coating resin is peeled off from the powder surface in some cases depending on the kind of dispersion medium, such as an oil agent used together with the copolymer, and thus it has been difficult to say that the effect of modifying the resin powder is sufficient.

Moreover, Patent Literature 2 describes that utilization of a copolymer obtained by copolymerizing monomer units containing a polymerizable silicone macromonomer having a particular structure makes it possible to impart to cosmetic materials the characteristics of the silicone polymer of having less stickiness, extending smoothly, giving a light feeling after use, and being rich in water repellency. However, according to studies conducted by the present inventor, there have been problems described below. In the method of coating the surface of a resin powder with the copolymer obtained by copolymerizing the monomer units containing a polymerizable silicone macromonomer, adsorption is not sufficient in some cases depending on the powder as is the same as described above and the coating resin is peeled off from the powder surface in some cases depending on the kind of dispersion medium, such as an oil agent used together with the copolymer, and thus it has been difficult to say that the effect of modifying the resin powder is sufficient. Moreover, in the method of adding to cosmetic materials a copolymer obtained by copolymerizing monomer units containing a polymerizable silicone macromonomer having a particular structure, the copolymer also acts simultaneously to another powder being contained in the cosmetic materials and having a high specific surface area and therefore cannot be adsorbed to the slippery surface of the spherical resin beads in a sufficient amount, and thus it has been difficult to say that the effect of modifying the resin powder is sufficient.

From the above-described circumstances, the present inventor has recognized that it is useful to develop resin beads: that are capable of imparting water repellency and oil repellency to products at a high level, and further, persistently over a long period of time; and, for example when used in cosmetic materials, that make it possible to realize a product in which makeup deterioration is hard to occur due to water or sweat and further, irrespective of the oil agent or the like used together with the resin beads.

The present invention has been completed in consideration of such circumstances, and accordingly, an object of the present invention is to provide resin beads, when used, for example, by being added to cosmetic materials and so on, which are capable of realizing imparting stable water repellency and oil repellency (hereinafter, sometimes referred to as "uniform water repellent and oil repellent effect") to products at a high level, more preferably which are capable of making the effect persistent over a long period of time, and which make it possible to achieve excellent persistence of makeup. Another object of the present invention is to provide a process for producing the resin beads, and yet another object of the present invention is to provide various kinds of products using the resin beads and having excellent properties.

Solution to Problem

The objects are achieved by the present invention described below. That is to say, the present invention provides resin beads being resin particles (a copolymer) obtained by subjecting a monomer mixture containing a plurality of monomers each having a copolymerizable functional group to suspension polymerization in a state where at least a non-polymerizable silicone is present, the resin particles containing the silicone in a fixed state.

Favorable embodiments of the resin beads include the following. That is to say, the favorable embodiments include: the resin beads in which the non-polymerizable silicone is any one of silicone-acrylic copolymers, polyether-modified silicones, polyether alkyl-modified silicones, trimethylsiloxysilicates, and silicone elastomers; the resin beads in which the monomer having a copolymerizable functional group is a (meth)acrylate-based monomer; the resin beads in which the monomer mixture contains a monomer having a plurality of copolymerizable functional groups and the content of the monomer is 20% by mass or more; the resin beads in which the non-polymerizable silicone is contained in a ratio of 0.1 to 50 parts by mass relative to 100 parts by mass of the resin particles; and the resin beads in which the resin particles have a volume average particle diameter of 20 μm or less.

The present invention provides, as another embodiment, a resin beads production process for producing the resin beads, including subjecting a polymerizable solution containing: a monomer mixture containing a plurality of monomers each having a copolymerizable functional group; a non-polymerizable silicone; and a polymerization initiator to suspension polymerization in an aqueous phase containing a dispersion stabilizer dissolved therein to produce resin particles containing the silicone in a fixed state and having both water repellency and oil repellency. The preferable embodiments include the method in which the monomer mixture contains a monomer having a plurality of copolymerizable functional groups and the content of the monomer is 20% by mass or more.

The present invention provides, as yet another embodiment, a water repellent and oil repellent product containing resin beads and being any one selected from the group consisting of cosmetics, dermal agents, paints, shaped articles, films, coating agents, dispersions, printing inks, inkjet inks and resin compositions, in which the resin beads are the resin beads according to any one of the above-described embodiments.

Advantageous Effects of Invention

According to the present invention, a non-polymerizable silicone is fixed inside resin beads, therefore sufficient water repellency and oil repellency are imparted to a product containing the resin beads added therein, and according to more suitable embodiments, such a product has excellent properties in that sufficient water repellency and oil repellency are imparted persistently over a long period of time. It is particularly effective that the resin beads according to suitable embodiments of the present invention are used in, for example, cosmetic materials because imparting a uniform water repellent and oil repellent effect persistently can be realized and excellent persistence of makeup is made possible.

DESCRIPTION OF EMBODIMENTS

Hereinafter, the present invention will be described in more detail giving preferable embodiments according to the present invention. The present inventor has conducted various studies in order to realize resin beads exhibiting a uniform water repellent and oil repellent effect to find that resin beads containing a non-polymerizable silicone that is contained in resin particles in a fixed state can realize more uniform and favorable water repellency and oil repellency, and according to suitable embodiments, can also realize imparting the water repellency and oil repellency persistently over a long period of time, and the problem in the conventional technology can be solved perfectly, and thus the present inventor has reached the present invention. Since the resin beads have the effect as described above, the resin beads, when applied to intended purposes such as, for example, cosmetic materials, exhibit excellent extensibility, have excellent extension and fitness to skin, can make the water repellency and oil repellency persistent, and therefore can reduce makeup deterioration due to water or body fat contained in sweat or the like.

The resin beads according to the present invention are resin particles obtained by subjecting a monomer mixture containing a plurality of monomers each having a copolymerizable functional group to suspension polymerization in a state where at least a non-polymerizable silicone is present, and the non-polymerizable silicone is fixed in the resin particles to be contained stably. The non-polymerizable silicone that constitutes the resin beads according to the present invention is not particularly limited as long as the silicone is non-polymerizable, and any of publicly known non-polymerizable silicones can be used. For example, a non-polymerizable silicone that is suitable for cosmetic materials, dermal agents such as ointments and medical patches, paints, shaped articles, films, coating agents, dispersions, printing inks, inkjet inks, or resin compositions may appropriately be used in consideration of the purpose of use. Non-polymerizable silicones that are used as a raw material for cosmetic materials are particularly suitable.

Specific examples of the non-polymerizable silicone for use in the present invention include the following. The examples include: modified silicones modified with various kinds of organic groups, such as polyether-modified silicones, polyester-modified silicones, acrylic modified silicones, polyether ester-modified silicones, polyether alkyl-modified silicones, polyether acrylic modified silicones, polyester acrylic modified silicones, polyglycerin-modified silicones, polyglycerin alkyl-modified silicones, phenyl-modified silicones, amino-modified silicones, carbinol-modified silicones, polyalkoxy-modified silicones, amino polyether-modified silicones, amide alkyl-modified silicones, aminoglycol-modified silicones, aminophenyl-modified silicones, polyether silicone/alkyl-comodified silicones, polyglycerin silicone/alkyl-comodified silicones and alkyl silicone commodified silicones; and polymers such as silicone-acrylic copolymers, silicone elastomers, trimethylsiloxysilicate-based silicones (silicone oils having a cross-linked structure), thermally denatured silicones, and polymeric silicones. Moreover, the structures of these non-polymerizable silicones may be linear, branched, or cyclic, these non-polymerizable silicones may be highly polymerized, may have a crosslinked structure, or may be produced through graft polymerization, and these non-polymerizable silicones may be used alone or in combination of two or more. Furthermore, according to studies conducted by the present inventor, publicly known non-polymerizable silicones excellent in applicability to cosmetic materials, such as silicone-acrylic copolymers, polyether-modified silicones, polyether alkyl-modified silicones, trimethylsiloxysilicate-based silicones, and silicone elastomers can be used more suitably among silicones, although the usability depends on the intended purpose.

The resin beads according to the present invention are resin particles (a copolymer) obtained by subjecting a monomer mixture containing a plurality of monomers each having a copolymerizable functional group to suspension polymerization in a state where at least the non-polymerizable silicone as described above is present. The resin component that constitutes the resin beads according to the present invention is not particularly limited, and any of publicly known resins can be used. For example, a resin that is suitable for cosmetic materials, dermal agents, paints, shaped articles, films, coating agents, dispersions, printing inks, inkjet inks, or resin compositions may appropriately be used in consideration of the purpose of use. Specific examples of the resin include (meth)acrylate-based resins, styrene-based resins, olefin-based resins, polyester-based resins, polyurethane-based resins, poly(thio)ether-based resins, polysulfone-based resins, polyimide-based resins, polycarbonate-based resins, polyamide-based resins, epoxy-based resins, phenol-based resins, melamine-based resins, ultraviolet ray-curable resins, polymers derived from natural products, thermally denatured silicone polymers, and thermoplastic elastomers.

Accordingly, the resin component of the resin beads according to the present invention may be any of polymers obtained by selecting a plurality of monomers for forming the above-described resin, the monomers each having a copolymerizable functional group, and then subjecting the monomers in combination to polymerization. Examples of more suitable monomers for use in the present invention having a copolymerizable functional group include multifunctional monomers and crosslinkable monomers each having a plurality of copolymerizable functional groups. The details of these monomers will be mentioned later. Moreover, according to studies conducted by the present inventor, monomers, such as (meth)acrylate, for forming acrylic-based resins that are excellent in applicability to cosmetic materials, such as transparency, are more preferable among the monomers having a copolymerizable functional group, although the usability depends on the intended purpose. Specifically, publicly known acrylic-based or methacrylic-based monomers can suitably be used, and among others, methacrylic-based monomers can be used more suitably. It is to be noted herein that the (meth)acrylate in the present specification means methacrylate or acrylate.

According to studies conducted by the present inventor, it is preferable that the resin component that constitutes the resin beads according to the present invention is constituted so as to contain 20% by mass or more, further preferably 25% by mass or more of a monomer having a plurality of copolymerizable functional groups in all the monomers used. As a matter of course, the monomer having a plurality of copolymerizable functional groups may constitute the whole amount of the monomers used. That is to say, by constituting the resin component as such, the resin beads formed through suspension polymerization, when used in, for example, cosmetic materials, contains the non-polymerizable silicone in a fixed state and the property of inhibiting the transfer of the non-polymerizable silicone is more improved, and therefore, with the resin beads, more uniform and favorable water repellency and oil repellency can be obtained, and the effect can be maintained more stably and persistently over a long period of time.

Examples of the monomer suitably used in the present invention and having a plurality of copolymerizable functional groups include copolymerizable multifunctional monomers and crosslinkable monomers, which are described below. As the copolymerizable multifunctional monomer or the crosslinkable monomer, general copolymerizable monomers containing a double bond adaptable to copolymerization are used. Examples of the monomer that is suitable for the present invention and is suitable for crosslinking include bifunctional (meth)acrylates such as ethylene glycol di(meth)acrylate, dipropylene glycol di(meth)acrylate, tripropylene glycol di(meth)acrylate, tetraethylene glycol di(meth)acrylate, butanediol di(meth)acrylate, hexanediol di(meth)acrylate, nonanediol di(meth)acrylate, tricyclodecane dimethanol di (meth)acrylate, modified bisphenol A di (meth)acrylate, and bisphenol A diglycidyl ether di(meth)acrylate.

Moreover, examples of the monomer include trifunctional (meth)acrylates such as pentaerythritol tri(meth)acrylate, trimethylolpropane tri(meth)acrylate, trimethylolpropane ethoxy tri(meth)acrylate, glycerin propoxy tri(meth)acrylate, tetrafunctional (meth)acrylates such as pentaerythritol tetra(meth)acrylate, pentaerythritol ethoxy tetra(meth)acrylate, and ditrimethylolpropane tetra(meth)acrylate, hexafunctional (meth)acrylates such as dipentaerythritol hexa(meth)acrylate, (meth)acrylates such as derivatives of these acrylates, oxetanes such as xylylene bisoxetane, 3-ethyl-3[[(3-ethyloxetane-3-yl)methoxy]methyl] oxetane, and furthermore, (meth)acrylate-modified compounds such as urethane di(meth)acrylate, urethane tri(meth)acrylate, polyester di(meth)acrylates, and polyester tri(meth)acrylates.

Moreover, according to studies conducted by the present inventor, it is preferable that the resin particles that constitute the resin beads according to the present invention contain the non-polymerizable silicone in a range described below. That is to say, it is preferable that the resin beads according to the present invention contain the non-polymerizable silicone in a ratio of 0.1 to 50 parts by mass relative to 100 parts by mass of the resin particles. It is not preferable that the ratio is less than 0.1 parts by mass because the extent of the exhibition of water repellent and oil repellent effect becomes small in some cases, and it is not preferable that the ratio exceeds 50 parts by mass because a remarkable effect cannot be expected despite an increase in the amount used and the resin beads are inferior in economic efficiency in some cases. It is preferable that the non-polymerizable silicone is contained in a ratio of 3 to 20 parts by mass relative to 100 parts by mass of the resin particles because of the balance between the content and the effect.

Moreover, according to studies conducted by the present inventor, the resin beads according to the present invention containing the above-described constituents may contain a pigment or the like in addition to the constituents. Examples of the pigment include metal oxides such as titanium oxide, zinc oxide, Bengal red, yellowish oxides, and iron black, certified colors such as Red No. 201 and Red No. 202, and carbon blacks. Moreover, the resin beads may contain an extender such as mica, talc, kaolin, or calcium carbonate, or a surface active agent or dispersant that disperses the pigment. Furthermore, the resin beads may contain an ultraviolet-absorbing component, and examples of the ultraviolet-absorbing component include fine particles of titanium dioxide, fine particles of zinc oxide, cinnamic acid-based ultraviolet absorbers and dibenzoylmethane-based ultraviolet absorbers.

Moreover, it is preferable that the resin beads according to the present invention containing these constituents are fine particles having a volume average particle diameter within a range of 20 μm or less, more preferably having a volume average particle diameter within a range of 15 μm or less. When the volume average particle diameter falls within the range, the resin beads according to the present invention can exhibit slipperiness and a soft focus property each being a property required, for example, as resin beads for cosmetic materials.

The process for producing the resin beads according to the present invention includes subjecting a polymerizable solution containing: a monomer mixture containing a plurality of monomers each having a copolymerizable functional group; a non-polymerizable silicone; and a polymerization initiator to suspension polymerization in an aqueous phase containing a dispersion stabilizer dissolved therein to produce resin particles containing the silicone in a fixed state. By constituting the process as such, the resin particles having both water repellency and oil repellency can stably be produced and resin beads that can exhibit a uniform water repellent and oil repellent effect can be obtained. It is to be noted that the "monomer mixture" specified in the present invention means that two or more monomers coexist during reaction, but, as will be described later, does not necessarily mean that a plurality of monomers are in a mixed state in advance. In the present invention, it is preferable to prepare an oil phase polymerizable solution for conducting suspension polymerization in an aqueous phase in the manner, for example, as described below to obtain the resin beads using the prepared oil phase polymerizable solution. First of all, the polymerizable solution to be an oil phase is prepared by adding and mixing, in advance, the monomer mixture, the non-polymerizable silicone, and the polymerization initiator, and an organic solvent as necessary. The resin beads according to the present invention containing the non-polymerizable silicone in a fixed state can stably and easily be obtained by subjecting the polymerizable solution thus prepared to suspension polymerization in the aqueous phase containing a dispersion stabilizer dissolved therein.

As the polymerization initiator for use in the present invention, any one of publicly known polymerization initiators may be used as long as the polymerization initiator can achieve the objects of the present invention. Specifically, the polymerization initiators as listed below can be used. Examples of the polymerization initiator include peroxide-based polymerization initiators such as a lauryl peroxide, a benzoyl peroxide, and t-butyl peroxy(2-ethylhexate) and azo compounds such as 2,2'-azobisisobutyronitrile, 2,2'-azobis(2,4-dimethylvarelonitrile), and alkyl esters of 2,2'-azobisisobutyric acid. These polymerization initiators may be used alone or in combination of two or more.

In the case where the organic solvent is used for the production process according to the present invention, any one of publicly known organic solvents can preferably be used. Examples of the organic solvent that can suitably be used in the present invention include the following compounds. For example, ester-based solvents such as ethyl acetate and butyl acetate, ketone-based solvents such as methyl ethyl ketone and methyl isobutyl ketone, alcohols such as n-butanol, ether-based solvents such as ethyl cellosolve, butyl cellosolve, and ethylene glycol diethyl ether, glycol ether-based solvents such as dipropylene glycol monomethyl ether, and glycol ester-based solvents such as propylene glycol monomethyl ether acetate can be used, though not being particularly limited thereto. These organic solvents may be used alone or in combination of two or more.

The suspension polymerization in the process for producing resin beads according to the present invention is conducted by mixing, under stirring, the polymerization solution having the above-described constitution into an aqueous medium (aqueous phase) obtained by dissolving a dispersion stabilizer (protective colloid) in deionized water. In conducting the suspension polymerization, the droplet diameter of suspension liquid in the polymerizable solution may be adjusted as necessary with an emulsification apparatus, such as a homogenizer. The droplet diameter of the suspension liquid in the polymerizable solution can easily be adjusted to a droplet diameter with which a droplet can be suspended by adjusting shear force by changing the number of revolutions of a homogenizer or the like, and as a result, the particle diameter of the resin particles obtained by conducting the suspension polymerization can appropriately be adjusted.

It is preferable to set the kind and concentration of the dispersion stabilizer not to cause trouble such as breakdown or unification of droplets of the suspension liquid prepared with a homogenizer or the like during droplet adjustment, during transportation to a polymerization apparatus, or during polymerization process. Examples of the dispersion stabilizer suitably used in the present invention include water-soluble polymers such as methyl cellulose, polyvinyl alcohols, and sodium acrylate, and inorganic salts such as hydroxyapatite, tribasic calcium phosphate, and calcium carbonate. These dispersion stabilizers may be used alone or in combination of two or more.

The resin beads according to the present invention are obtained by heating the suspension liquid thus obtained at a temperature of 60 to 80° C. for 3 to 10 hours to conduct suspension polymerization. Further, after removing the dispersion stabilizer and so on through a cleaning process, the resin beads are peptized and dispersed in deionized water or the like and dissolved substances are removed through the washing process again, cleaning is repeated if necessary, and thereafter the resultant mixture is dried. Particles obtained in an aggregated state are crushed to obtain powdery resin beads.

EXAMPLES

Hereinafter, the present invention will be described in more detail giving Examples and Comparative Examples, however the present invention is not limited by the following Examples. In addition, "parts" or "%" below is based on mass.

In Examples and Comparative Examples, a partially saponified polyvinyl alcohol was used as a dispersion stabilizer constituting an aqueous phase of suspension polymerization and an azo compound was used as a polymerization initiator unless otherwise noted. Specifically, Poval 205 (trade name) being a partially saponified polyvinyl alcohol (hereinafter, abbreviated as "PVA") and manufactured by Kuraray Co., Ltd. was used as the dispersion stabilizer, and V-65 being 2,2'-azobis(2,4-dimethylvarelonitrile) and manufactured by Wako Pure Chemical Industries, Ltd. (hereinafter, abbreviated as "V-65") was used as the polymerization initiator.

Example 1

Example of Production with Polymerizable Monomer Liquid Containing Non-Polymerizable Silicone-Acrylic Copolymer First of all, to a solution prepared in advance and obtained by dissolving 4 parts of V-65 in 200 parts of a polyethylene glycol dimethacrylate (trade name: NK 1G, manufactured by Shin-Nakamura Chemical Co., Ltd.), 200 parts of lauryl methacrylate (trade name: LMA, manufactured by Kao Corporation) and 20 parts of a non-polymerizable silicone-acrylic copolymer (trade name: KP-578, active ingredient of 100%, manufactured by Shin-Etsu Chemical Co., Ltd) were added, and the resultant mixture was uniformly stirred and mixed to prepare a polymerizable monomer liquid. KP-578 used above is a graft polymer containing an acrylic polymer and a dimethylpolysiloxane.

Subsequently, in another container, the polymerizable monomer liquid prepared above was added and mixed to an aqueous phase obtained by dissolving 80 parts of PVA as a dispersion stabilizer in 1600 parts of ion-exchanged water, and the resultant mixture was stirred with a dissolver at 2500 rpm for 5 minutes and then further stirred with a homogenizer at 8000 rpm for 5 minutes to obtain a uniform suspension liquid.

Subsequently, in a reaction can of a polymerization apparatus provided with a stirrer and a nitrogen gas-introducing pipe, the suspension liquid obtained above was charged and subjected to polymerization reaction at 70° C. for 6 hours continuously. After cooling, fine resin particles produced from the suspension liquid were filtered and washed. The resin beads thus obtained were re-peptized in ion-exchanged water, and then the fine particles were filtered from the suspension liquid and were washed. Further, the fine particles were dried and crushed to obtain resin beads containing a non-polymerizable silicone in a fixed state.

Example 2

Example of Production with Polymerizable Monomer Liquid Containing Non-Polymerizable Polyether-Alkyl Co-Modified Silicone First of all, 200 parts of a modified bisphenol diacrylate (trade name: EBECRYL 150, manufactured by Daicel-Allnex Ltd.), 80 parts of a non-polymerizable polyether-alkyl co-modified silicone (trade name: KSG-310, active ingredients of 25 to 35%, manufactured by Shin-Etsu Chemical Co., Ltd.), and a solution prepared in advance and obtained by dissolving 4 parts of V-65 in 20 parts of propylene glycol monomethyl ether acetate were added to 200 parts of hexanediol diacrylate (trade name: HDDA, manufactured by Daicel-Allnex Ltd.). And the resultant mixture was uniformly stirred and mixed to prepare a polymerizable monomer liquid. Subsequently, in another container, resin beads containing a non-polymerizable silicone in a fixed state were obtained by the same operations, such as washing after polymerization, as in Example 1 except that polymerization was conducted using an aqueous phase obtained by dissolving 88 parts of PVA as a dispersion stabilizer in 1600 parts of ion-exchanged water. KSG-310 used above is a mixture of mineral oil and 25 to 35% of a polyether-alkyl co-modified silicone and is a material that has been used for cosmetics.

Example 3

Example of Production with Polymerizable Monomer Liquid Containing Non-Polymerizable Trimethylsiloxysilicate Resin beads containing a non-polymerizable silicone in a fixed state were obtained by the same operations as in Example 1 except that 280 parts of lauryl methacrylate (trade name: LMA, manufactured by Kao Corporation) and 40 parts of a non-polymerizable trimethylsiloxysilicate (trade name: X-21-5250, active ingredients of 50%, manufactured by Shin-Etsu Chemical Co., Ltd.) were added to a solution prepared in advance and obtained by dissolving 4 parts of V-65 in 120 parts of a polyethylene glycol dimethacrylate (trade name: NK 1G, manufactured by Shin-Nakamura Chemical Co., Ltd.), and the resultant mixture was uniformly stirred and mixed to prepare a polymerizable monomer liquid. In addition, X-21-5250 used above is a mixture of 50% of a trimethylsiloxysilicate and 50% of cyclopentasiloxane being a cyclic silicone oil.

Example 4

Example of Production with Polymerizable Monomer Liquid Containing Non-Polymerizable Silicone Elastomer Resin beads containing a non-polymerizable silicone in a fixed state were obtained by the same operations as in Example 1 except that 200 parts of lauryl methacrylate (trade name: LMA, manufactured by Kao Corporation) and 150 parts of a non-polymerizable silicone elastomer (trade name: 9040 S. E. B., active ingredients of 12%, manufactured by Dow Corning Toray Co. , Ltd.) were added to a solution prepared in advance and obtained by dissolving 4 parts of V-65 in 200 parts of a polyethylene glycol dimethacrylate (trade name: NK 1G, manufactured by Shin-Nakamura Chemical Co., Ltd.), and the resultant mixture was uniformly stirred and mixed to prepare a polymerizable monomer liquid. The silicone elastomer (trade name: 9040 S.E.B.) used above is a mixture of 12% of a dimethicone crosspolymer and 88% of cyclopentasiloxane.

Example 5

Example of Production with Polymerizable Monomer Liquid Containing Non-Polymerizable Polyether Co-Modified Silicone Resin beads containing a non-polymerizable silicone in a fixed state were obtained by the same operations as in Example 1 except that 200 parts of lauryl methacrylate (trade name: LMA, manufactured by Kao Corporation) and 28 parts of a non-polymerizable polyether co-modified silicone (trade name: KF-6015, active ingredients of 100%, manufactured by Shin-Etsu Chemical Co., Ltd.) were added to a solution prepared in advance and obtained by dissolving 4 parts of V-65 in 200 parts of a polyethylene glycol dimethacrylate (trade name: NK 1G, manufactured by Shin-Nakamura Chemical Co., Ltd.), and the resultant mixture was uniformly stirred and mixed to prepare a polymerizable monomer liquid.

Example 6

Example of Production with Polymerizable Monomer Liquid Containing: 18% by Mass of Monomer Having Plurality of Copolymerizable Functional Groups; And Non-Polymerizable Silicone Elastomer Resin beads containing a non-polymerizable silicone in a fixed state were obtained by the same operations as in Example 1 except that 328 parts of lauryl methacrylate (trade name: LMA, manufactured by Kao Corporation) and 150 parts of a non-polymerizable silicone elastomer (trade name: 9040 S. E. B., active ingredients of 12%, manufactured by Dow Corning Toray Co., Ltd.) were added to a solution prepared in advance and obtained by dissolving 4 parts of V-65 in 72 parts of a polyethylene glycol dimethacrylate (trade name: NK 1G, manufactured by Shin-Nakamura Chemical Co., Ltd.), and the resultant mixture was uniformly stirred and mixed to prepare a polymerizable monomer liquid.

Comparative Example 1

Example of Polymerizable Monomer Liquid Not Containing Silicone

Resin beads not containing silicone were obtained by the same operations as in Example 1 except that 200 parts of lauryl methacrylate (trade name: LMA, manufactured by Kao Corporation) was added to a solution prepared in advance and obtained by dissolving 4 parts of V-65 in 200 parts of a polyethylene glycol dimethacrylate (trade name: NK 1G, manufactured by Shin-Nakamura Chemical Co., Ltd.), which was the same solution as used in Example 1, and the resultant mixture was uniformly stirred and mixed to prepare a polymerizable monomer liquid.

Comparative Example 2

Example of Applying Coating Treatment to Beads of Comparative Example 1

Into a Henschel mixer, 100 parts of the resin beads obtained in Comparative Example 1 were charged, then a solution prepared in advance and obtained by dissolving 5 parts of the silicone-acrylic copolymer (trade name: KP-578, active ingredients of 100%, manufactured by Shin-Etsu Chemical Co., Ltd.) used in Example 1 in 5 parts of isopropyl alcohol was injected into the mixer, and the resultant mixture was uniformly stirred and mixed and thereafter dried and crushed to obtain resin beads the surfaces of which were coated with silicone.

<Evaluation>

The volume average particle diameter for resin beads of each of Examples and Comparative Examples was measured, and further, the water repellency and the oil repellency were evaluated in the following manner.

(Measurement of Volume Average Particle Diameter)

The volume average particle diameter of resin beads prepared in each of Examples 1 to 6 and Comparative Examples 1 and 2 was measured with a Coulter counter (manufactured by Beckman Coulter, Inc.). Obtained results are shown together in Table 1.

(Evaluation of Water Repellency)

The water repellency for resin beads prepared in each of Examples 1 to 6 and Comparative Examples 1 and 2 was observed in the following manner and evaluated according to the following criteria. Specifically, 20 ml of ion-exchanged water was put in a 50 ml test tube, and 0.5 g of resin beads were added thereto and then lightly stirred with a spatula. And whether the resin beads were floating on the surface of water or not was observed after 1 hour and the water repellency was evaluated by the precipitation state of the resin beads. Evaluation was conducted according to the evaluation criteria in which the state where the resin beads were completely floating was ranked as A, the state where part of the resin beads precipitated was ranked as B, and the state where most of the resin beads precipitated was ranked as C. Furthermore, the sustainability of the effect was evaluated by also observing the state after 1 day in order to check the stability of a water repellency-imparting effect with the elapsed time. The results are shown together in Table 1.

(Evaluation of Oil Repellency)

The oil repellency for resin beads prepared in each of Examples 1 to 6 and Comparative Examples 1 and 2 was observed in the following manner and evaluated according to the following criteria. Specifically, 20 ml of olive squalene was put in a 50 ml test tube, and 0.5 g of resin beads were added thereto and then lightly stirred with a spatula. And whether the resin beads were floating on the surface of squalene or not was observed after 1 hour and the oil repellency was evaluated by the precipitation state of the resin beads. Evaluation was conducted according to the evaluation criteria in which the state where the resin beads were completely floating was ranked as A, the state where part of the resin beads precipitated was ranked as B, and the state where most of the resin beads precipitated was ranked as C. Furthermore, the sustainability of the effect was evaluated by also observing the state after 1 day in order to check the stability of an oil repellency-imparting effect with the elapsed time. The results are shown together in Table 1.

TABLE 1

Evaluation results of particle diameter, water repellency, and oil repellency for resin beads of Examples and Comparative Examples

| | Silicone | Average particle diameter (µm) | Water repellent effect | | Oil repellent effect | |
|---|---|---|---|---|---|---|
| | | | After 1 hour | After 1 day | After 1 hour | After 1 day |
| Example 1 | Silicone-acrylic copolymer | 10.1 | A | A | A | A |
| Example 2 | Polyether-alkyl co-modified silicone | 9.7 | A | A | A | A |
| Example 3 | Mixture of trimethylsiloxysilicates | 10.2 | A | A | A | A |
| Example 4 | Silicone elastomer | 9.6 | A | A | A | A |

TABLE 1-continued

Evaluation results of particle diameter, water repellency, and oil repellency for resin beads of Examples and Comparative Examples

| | Silicone | Average particle diameter (μm) | Water repellent effect After 1 hour | Water repellent effect After 1 day | Oil repellent effect After 1 hour | Oil repellent effect After 1 day |
|---|---|---|---|---|---|---|
| Example 5 | Polyether co-modified silicone | 8.3 | A | A | A | A |
| Example 6 | Silicone elastomer | 8.0 | A | B | A | B |
| Comparative Example 1 | — | 10.1 | C | C | C | C |
| Comparative Example 2 | Coating with silicone-acrylic copolymer | 10.1 | B | B | B | C |

(Use in Cosmetic Material)

Cosmetic materials of Examples 7 to 12 and Comparative Examples 3 and 4 were produced with respective components shown in Table 2 and the resin beads obtained in Examples and Comparative Examples blended in an amount as described in Table 2, and usability thereof was evaluated. Specifically, the cosmetic materials were produced in the following manner. Each of silicone-treated powders described in Table 2 (mica, talc, fine particles of titanium oxide, and barium sulfate) and resin beads of each of Examples and Comparative Examples were blended in an amount as described in Table 2, and the resultant mixture was mixed until the mixture became uniform to prepare a powder mixture. And a mixture prepared in advance by mixing vaseline, squalene, and glyceryl trioctanoate was added to the powder mixture, and the resultant mixture was mixed until the mixture became uniform. Subsequently, the resultant mixture was filled in a container, and was subjected to press molding as necessary to obtain a cosmetic material. Using the cosmetic material, the usability with respect to the items shown in Table 3 was evaluated according to the evaluation criteria shown in Table 3, and the results are also shown in Table 3.

TABLE 2

Composition of cosmetic materials (parts by mass)

| Components | Amount blended |
|---|---|
| Vaseline | 2.5 |
| Squalene | 3.0 |
| Glyceryl trioctanoate | 2.0 |
| Silicone-treated mica | 40.0 |
| Silicone-treated talc | 33.0 |
| Fine particles of silicone-treated titanium oxide | 5.0 |
| Silicone-treated barium sulfate | 10.0 |
| Resin beads of Examples 1 to 6 and Comparative Examples 1 and 2 | 4.5 |

TABLE 3

Evaluation Results

| Resin beads used | Example of cosmetic material | Extension to skin | Fitness | Non-Stickiness | Persistence of makeup |
|---|---|---|---|---|---|
| Example 1 | Example 7 | A | A | A | A |
| Example 2 | Example 8 | A | A | A | A |
| Example 3 | Example 9 | A | A | A | A |
| Example 4 | Example 10 | A | A | A | A |
| Example 5 | Example 11 | A | A | A | A |
| Example 6 | Example 12 | B | B | C | C |
| Comparative Example 1 | Comparative Example 3 | B | C | D | D |
| Comparative Example 2 | Comparative Example 4 | B | B | C | D |

(Evaluation Results) A: Excellent, B: Good, C: Fair, D: Poor (Evaluation Results)

It was able to be confirmed that all of the resin beads of Examples 1 to 5 had more favorable water repellency and oil repellency and had more excellent stability with the elapsed time over a long period of time when the resin beads of Examples 1 to 6 were compared with the resin beads of Comparative Examples 1 and 2. Moreover, the cosmetic materials of Examples 7 to 11, which were produced using the resin beads of Examples 1 to 5 respectively, particularly had less stickiness, lighter extensibility and spreadability, better fitness, and better persistence of makeup when compared with the cosmetic materials of Comparative Examples 3 and 4, which were produced using the resin beads of Comparative Examples 1 and 2 respectively. Moreover, it was found that the resin beads of Example 6, in which the content of the monomer having a plurality of copolymerizable functional groups was less than 20% by mass, had water repellency-imparting effect and oil repellency-imparting effect, but was inferior particularly in stability of those effects with the elapsed time over a long period of time when compared with the resin beads of Examples 1 to 5. As a result, in the case where the present invention is applied to cosmetics, it was confirmed that cosmetics exhibiting favorable water repellency and oil repellency were able to be obtained by using the resin beads of Examples 1 to 6, and that cosmetics having a favorable persistence of makeup were able to be obtained particularly by using the resin beads of Examples 1 to 5. Moreover, similarly, by using the resin beads according to the present invention for products, such as dermal agents including ointments and medical patches, paints, shaped articles, films, coating agents, dispersions, printing inks, inkjet inks, and resin compositions, stable water repellency and oil repellency can be imparted to the products at a high level to find that the resin beads according to the present invention is useful.

INDUSTRIAL APPLICABILITY

Use of the resin beads according to the present invention in, for example, cosmetic materials makes it possible to obtain products having both water repellency and oil repellency and realizing a favorable persistence of makeup. Accordingly, the resin beads according to the present invention are most suitable for use in the fields that need such properties and functions, such as, for example, cosmetics, dermal agents, paints, shaped articles, films, coating agents, dispersions, printing inks, inkjet inks, and resin compositions, and use of the resin beads according to the present invention in a wide variety of intended purposes is expected.

The invention claimed is:

1. Resin beads being resin particles comprising a non-polymerizable silicone in a fixed state,
   - wherein the resin particles are a product of suspension polymerization of a monomer mixture comprising a plurality of monomers each having a copolymerizable functional group, in the presence of at least the non-polymerizable silicone,
   - the non-polymerizable silicone is at least one material selected from the group consisting of silicone-acrylic copolymers, polyether-modified silicones, polyether alkyl-modified silicones, trimethylsiloxysilicates, and silicone elastomers, and
   - at least 20% by mass of the monomer having a copolymerizable functional group in the monomer mixture is a monomer having a plurality of copolymerizable functional groups.

2. The resin beads according to claim 1,
   - wherein the monomer having a copolymerizable functional group is a (meth)acrylate-based monomer.

3. The resin beads according to claim 1,
   - wherein the non-polymerizable silicone is contained in a ratio of 0.1 to 50 parts by mass relative to 100 parts by mass of the resin particles.

4. The resin beads according to claim 1,
   - wherein the resin particles have a volume average particle diameter of 20 μm or less.

5. A resin beads production process for producing the resin beads according to claim 1, comprising:
   - subjecting a polymerizable solution comprising: the monomer mixture comprising the plurality of monomers each having a copolymerizable functional group; the non-polymerizable silicone; and a polymerization initiator, to the suspension polymerization in an aqueous phase,
   - wherein the aqueous phase comprises a dispersion stabilizer dissolved therein so as to produce the resin particles comprising the non-polymerizable silicone in the fixed state and having both water repellency and oil repellency.

6. A water repellent and oil repellent product comprising the resin beads according to claim 1,
   - wherein the water repellent and oil repellent product is at least one product selected from the group consisting of cosmetics, dermal agents, paints, shaped articles, films, coating agents, dispersions, printing inks, inkjet inks and resin compositions.

* * * * *